(12) United States Patent
Bacon

(10) Patent No.: US 8,600,772 B2
(45) Date of Patent: Dec. 3, 2013

(54) SYSTEMS AND METHODS FOR INTERFACING WITH HEALTHCARE ORGANIZATION CODING SYSTEM

(75) Inventor: David R. Bacon, Sandy, UT (US)

(73) Assignee: 3M Innovative Properties Company, Saint Paul, MN (US)

( * ) Notice: Subject to any disclaimer, the term of this patent is extended or adjusted under 35 U.S.C. 154(b) by 517 days.

(21) Appl. No.: 12/473,975

(22) Filed: May 28, 2009

(65) Prior Publication Data

US 2010/0306218 A1    Dec. 2, 2010

(51) Int. Cl.
*G06F 19/00*    (2011.01)
*G06Q 10/00*    (2012.01)

(52) U.S. Cl.
USPC .................................... 705/2; 705/3

(58) Field of Classification Search
USPC ...................................... 705/2, 3, 4
See application file for complete search history.

(56) References Cited

U.S. PATENT DOCUMENTS

| | | | |
|---|---|---|---|
| 6,055,494 A | 4/2000 | Friedman | |
| 6,182,029 B1 | 1/2001 | Friedman | |
| 6,292,771 B1 | 9/2001 | Haug et al. | |
| 6,556,964 B2 | 4/2003 | Haug et al. | |
| 6,915,254 B1 | 7/2005 | Heinze et al. | |
| 7,233,938 B2 | 6/2007 | Carus et al. | |
| 7,610,192 B1 | 10/2009 | Jamieson | |
| 2004/0073458 A1 | 4/2004 | Jensen | |
| 2004/0172297 A1 | 9/2004 | Rao et al. | |
| 2004/0220831 A1 | 11/2004 | Fabricant | |
| 2004/0243545 A1 | 12/2004 | Boone et al. | |
| 2005/0120020 A1 | 6/2005 | Carus et al. | |
| 2005/0137910 A1 | 6/2005 | Rao et al. | |
| 2005/0240439 A1* | 10/2005 | Covit et al. ..................... | 705/2 |
| 2006/0095294 A1 | 5/2006 | Compton et al. | |
| 2006/0106795 A1 | 5/2006 | Compton et al. | |
| 2006/0129435 A1 | 6/2006 | Smitherman et al. | |
| 2007/0233660 A1 | 10/2007 | Rogers | |
| 2008/0004505 A1 | 1/2008 | Kapit et al. | |
| 2008/0288292 A1 | 11/2008 | Bi et al. | |

FOREIGN PATENT DOCUMENTS

WO    2007/136852 A2    11/2007

* cited by examiner

*Primary Examiner* — Sean K Hunter
(74) *Attorney, Agent, or Firm* — Steven A. Bern

(57) ABSTRACT

Systems, articles, and methods for assisting medical coders with review and identification of relevant portions of electronic documents associated with a patient's encounter with a healthcare organization, and for the inputting of codes describing said encounter.

36 Claims, 10 Drawing Sheets

Fig. 5

SYSTEMS AND METHODS FOR INTERFACING WITH HEALTHCARE ORGANIZATION CODING SYSTEM

BACKGROUND

In order for healthcare organizations to receive remuneration from payment organizations (such as insurers or the government) for services provided to a patient, payment requests need be submitted to the payment organizations. These payment requests describe services provided to the patient via a set of standardized codes. The payment organization reviews the codes and then makes a payment.

To represent the healthcare organization's services via codes, a medical coder reviews documents generated in association with the healthcare organization's encounter with the patient. Often these documents are generated by doctors or other healthcare professionals that interact with and provide services to the patient. Examples of such documents include a discharge summary or an operative report. Complex patient encounters (such as a difficult surgery) might yield dozens of documents, each of which will be reviewed by the medical coder. Many of these documents do not adhere to particular formatting. Some of the documents are hand written, or scanned.

Medical coders review these documents and identify billable aspects of the patient encounter, and then associate these billable aspects with codes. This review process, which includes reading, navigating, and assessing documentation, is cumbersome, sometimes requiring up to 70% of a medical coder's time.

SUMMARY

Systems and methods for interfacing with a healthcare organization's coding system are provided herein. In certain embodiments, these systems and methods may facilitate faster access to relevant information for a coder, and the elimination of review of irrelevant information.

In one embodiment, a computer-implemented method is described, the method comprising: receiving electronic documents associated with a patient's encounter with a healthcare organization; identifying terms in the electronic documents that are relevant to the patient's diagnosis or a procedure associated with the patient, wherein identifying terms comprises comparing terms within the electronic document to terms in a database of terms; and, displaying in a user interface at least portions of at least one of the electronic documents with first visual indicia associated with the identified terms.

In another embodiment, a computer-readable medium is described, the computer-readable medium comprising application code which implements the following procedures when executed by a computer: generating in a user interface an application window; displaying within the application window subsets of at least two medical documents, the two medical documents having been generated in association with a patient's encounter with a healthcare organization; matching terms found within the subsets with terms that exist within a database of terms pre-identified as being relevant to medical coding; and, associating matched terms with a first visual indicia, and for the matched terms displayed within the application window, displaying the matched terms with associated first visual indicia.

In another embodiment, a system is described, the system comprising one or more microprocessors and memory, which executes software to cause the system to: receive electronic documents associated with a patient's encounter with a healthcare organization; identify terms in the electronic documents that are relevant to the patient's diagnosis or a procedure associated with the patient, wherein identifying terms comprises comparing terms within the electronic document to terms in a database of terms; and, display in a user interface at least portions of at least one of the electronic document with first visual indicia associated with the identified terms.

BRIEF DESCRIPTION OF DRAWINGS

FIG. 5 is a screenshot from a user interface of the MDAE system.

DETAILED DESCRIPTION

Figure 1:
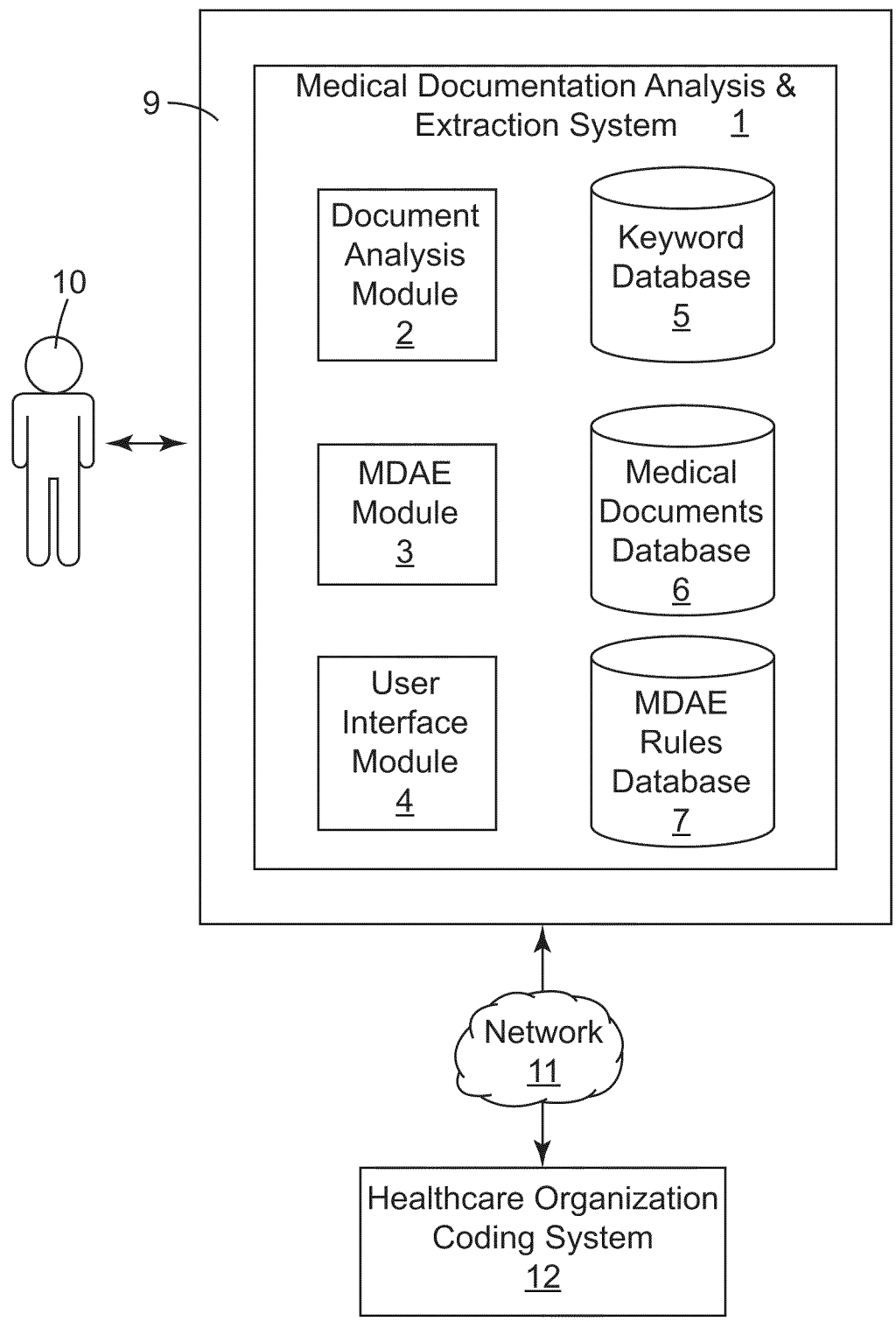
FIG. 1 is a diagram showing systems that might be used by a healthcare organization, including one embodiment of the Medical Documentation Analysis and Extraction (MDAE) system.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

A coding and reimbursement system is a computer software-based system used by a medical coder to describe a patient's encounter with a healthcare organization in a standardized manner. Coding and reimbursement systems utilize a defined set of codes, which associate procedures or diagnosis with particular alpha-numeric codes. The most important set of such codes, and the one most coding and reimbursement systems are based upon, is the International Classification of Diseases (ICD) published by the World Health Organization. The ICD uses six-character codes to classify diseases and a wide variety of signs, symptoms, abnormal findings, complaints, social circumstances and external causes of injury or disease. The ICD is updated periodically, the current version being referred to as ICD-9-CM. Modern versions of the ICD also include codes used to classify procedures.

The ICD is a hierarchy of diseases and procedures. For example, the ICD-9 code for pneumonia is 486; bacterial pneumonia (a type of pneumonia) has the code 482.9. Currently available coding and reimbursement systems take different approaches in how a coder navigates through the ICD hierarchy to arrive at a specific disease code. Some systems employ a code look-up approach whereby a coder identifies the diagnosis code, and is then presented with sub-code selections that are associated with the diagnosis. In the case of pneumonia, upon a coder selecting ICD code 486, he or she would be presented with the several more specific coding choices associated with pneumonia (for example, bacterial, aspiration, or anthrax). The coder would than choose the appropriate codes based on what is documented in the system.

Another approach to coding is termed the clinical approach, which involves asking questions that are related to ICD-defined diagnosis and procedures. The coder would initially identify pneumonia, just as with the code look-up approach mentioned above. Then, rather than being presented with sub-selections, the clinical approach would involve a computer system asking questions. For example, the computer system would ask the coder if the patient had bacterial, aspiration, inhalation or any other condition associated with pneumonia. If the coder selected bacterial, the system would ask the coder what the bacterial pneumonia was due to, and present possibilities like hemophilus influenza, mixed bacterial, or streptococcus. This approach helps the coder ensure that they are coding all associated conditions and procedures associated with the patients care.

FIG. 1 is a diagram showing representative systems that might be used by a healthcare organization. Healthcare organization coding system 12 may be one of several commercially available coding systems. One such coding system is that which is marketed by 3M™ Health Information Systems of Salt Lake City, Utah under the trade name "3M™ Coding & Reimbursement System". The healthcare organization coding system 12 facilitates the process of representing a patient's encounter with a healthcare organization via codes, which can then be submitted to a payment organization, such as an insurer or the government, for review and payment. Healthcare organization coding system 12 may have one or more interfaces to interact with a coder, such as coder 10. In the example shown in FIG. 1, this interface is the medical documentation analysis and extraction system ("MDAE system") 1, which will be described in greater detail below. However, instead of or in addition to the MDAE system, other interfaces could exist. For example, healthcare organization coding system 12 may provide a web-based interface where coder 10 can access and enter codes that define aspects of a patient's encounter with the healthcare organization. Alternatively, healthcare organization coding system 12 could provide its own graphical user interface. In various embodiments, the healthcare organization coding system may support a plurality of such interfaces.

Coder 10 is typically an individual employed by the healthcare organization to review medical documentation associated with a patient's encounter with the healthcare organization, and then represent billable aspects of the encounter in codes recognized by payment organizations. Payment organizations are typically insurers or government institutions. MDEA 1 provides an improved way for coder 10 to interact with healthcare organization coding system 12. Coder 10 uses a keyboard and other input devices (such as a pointing device such as a mouse or a touch screen) to interact with MDEA system 1.

MDEA system 1 is shown as software being executed on physical computer system 9. The software is contained on a computer-readable medium such as a hard drive, computer memory, a CD-ROM, a DVD, or any other computer-readable medium. Physical computer system 9 may be any computer having a processor and memory. In one embodiment, physical computer system 9 is a personal computer. In another embodiment it is a sever computer that interacts with coder 10 in a client/server type computing environment (this architecture is not depicted in FIG. 1). Though shown residing on one physical computing system 9, other embodiments may have various components of the MDAE system 1 operating on different, communicatively coupled computers. Physical computer system 9 includes an operating system (not shown in FIG. 1) to allocate processing, memory, network, and other computing resources to MDAE system 1.

MDEA system 1 includes a number of functional and storage modules. The functionality of the functional modules will be described in greater detail later in this description. At a high level, however, MDAE module 3 controls the other MDAE modules, and controls functionality described herein not tied to any other module. MDAE module 3 facilitates retrieving medical documentation of various types from various databases associated with the healthcare organization. Medical documentation is placed in storage module medical documentation database 6. Medical documentation database 6, and other databases referred to herein, may be any type of data storage and retrieval system, such as flat files, an object-oriented database, or a relational database system.

With documents in the medical documents database 6, MDAE module 3 may invoke document analysis module 2. For a given patient's encounter with a healthcare organization, document analysis module 2 iterates through associated documentation in the medical documentation database 6. Document analysis module 2 has two principle objectives.

First, document analysis module 2 identifies portions of documents that have been pre-defined to be of particular relevance to coder 10. This pre-definition takes the form of rules stored in MDAE rules database 9, which are accessed by document analysis module 2. A rule might declare that medical documents having certain attributes are more (or less) relevant to coders than others. The rules might further declare that portions of documents having particular attributes are of higher relevance. In the end, application of the rules from MDAE rules database 7 yields data defining subsets of the medical documents.

Second, document analysis module 2 iterates through the subsets of documents and compares terms found in the medical documents to terms found in keyword database 5. Keyword database 5 is a database having keywords (including phrases) as well as other information specific to one or more ICD codes. For example, if a particular term is found, that term may be suggestive of a particular ICD code. This information is associated with the term. In one embodiment, this association is facilitated by creating an new version the document in a markup language that allows for the imbedding of metadata with terms, such as HTML, or some variant of XML.

When the medical documentation has been analyzed by document analysis module 2, the document is passed by MDAE module 3 to user interface module 4, to display identified document subsets, with various visual indicia associated with identified terms. Additionally, functionality is provided such that, in one embodiment, upon coder 10 selecting the term (such as clicking it or visual indicia associated with it), the healthcare organization coding system 12 is invoked, and coder 10 is places as far into the coding hierarchy as is possible. This saves coder time, and reduces the chance of coder error because there are fewer selections that need to be made by the coder.

Figure 2:
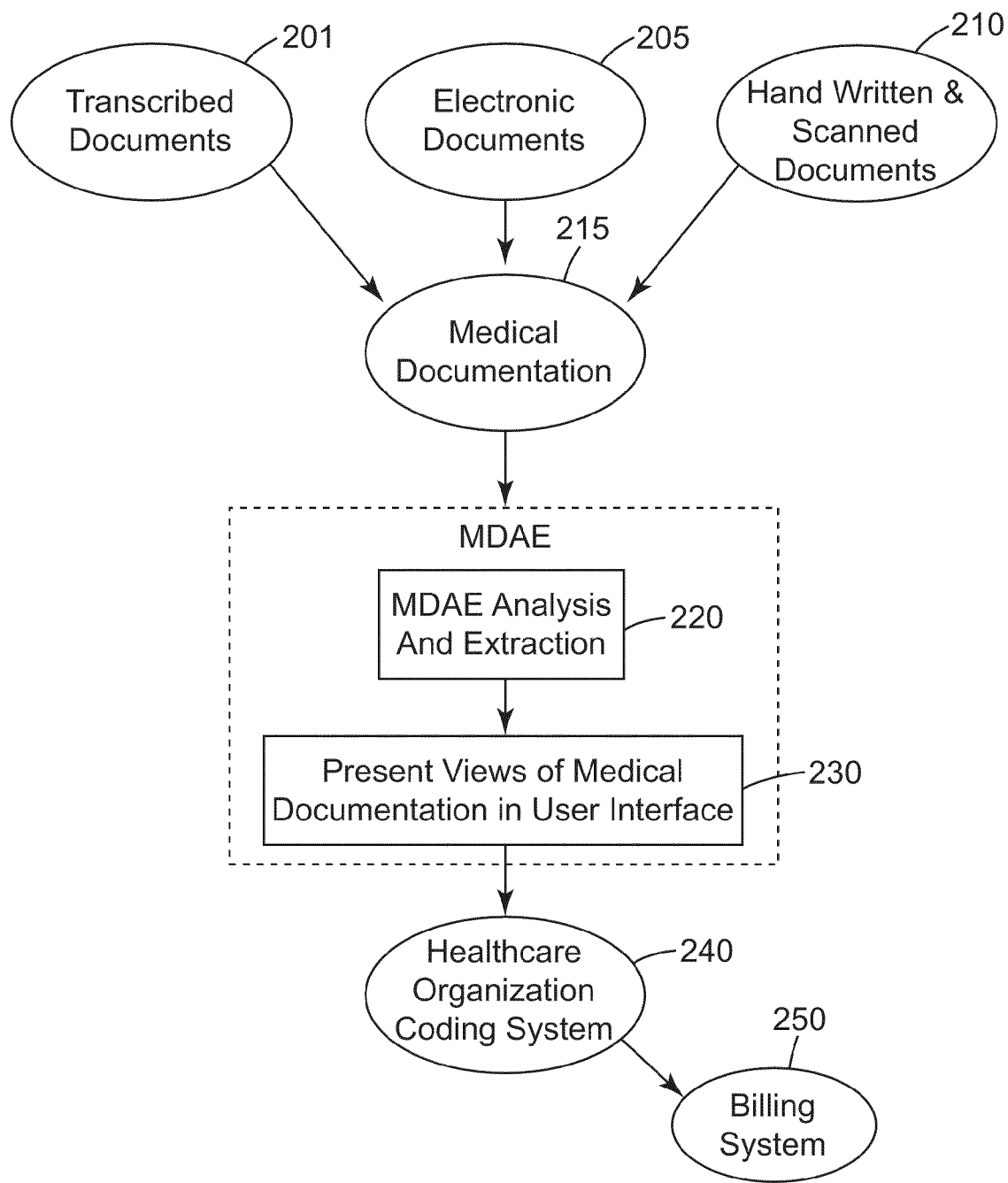
FIG. 2 is a high-level flowchart showing functionality of the MDAE system.

FIG. 2 is a high-level flowchart showing functionality of the MDAE system. Documents having information concerning a patient's interaction with a healthcare organization identified. These documents could take various forms. For example, they could be transcribed documents (201), electronic documents (205), or even handwritten and scanned documents (210). Collectively, these document sets comprise medical documentation 215 that could be relevant to coder 10 for coding billable aspects of the patient's interaction with the healthcare organization. Medical documentation 215 may include the patient's history and physical, physician and nursing progress notes, ancillary reports (laboratory, radiology, and so forth) and a discharge summary that describes the complete patient's stay. In an example later used in this description, medical documentation includes a discharge summary, emergency report and several consultation reports. It is not necessary for the medical documentation 215 to be located on a single place or on a single database system. As will be seen in subsequent discussion of the MDAE system, an initial procedure of the MDAE system is to retrieve medical documentation. This procedure may be customized to the environment in which the MDAE system is configured, and will often in practice mean retrieval from several different disparately located systems.

Once the MDAE system has access to medical documents 215, it proceeds with two high-level process steps. The first high-level process step comprises analysis and extraction (220). This will be discussed in further detail below, but generally comprises iterating through the medical documentation and identifying portions of the medical documents 215 that are relevant to coding, as well as, within those portions of the documents, terms relevant to coding. Once the analysis and extraction step is completed, the identified portions (and associated relevant terms) of the medical documents 215 are displayed in a user interface (230) to coder 10. Various functions are further provided along with the display in the user interface. For example, identified terms are presented with visual indicia (such as highlighting or coloring) to direct a coder's attention to the terms, and the terms may be selected, by for example clicking with a pointing device. Once a term is selected, the MDAE system invokes the healthcare organization coding system 12 (step 240), automatically providing to the healthcare organization coding system 12 coding relevant details. This allows coder 10 to avoid the otherwise necessary process steps of drilling down to a specific code from a number of high level general code descriptions. For example, in some cases, the information identified by the MDAE system, and provided to the healthcare organization coding system 12 upon selection of a term with in the MDAE's user interface, is sufficient for healthcare organization coding system 12 to directly identify a specific code. In other cases, however, there is still not enough information to identify a specific code, but there is enough information to identify general categories of relevant codes, and thus place coder 10 further down the coding hierarchy than she would otherwise be had she not had the MDAE system. Once the proper code is identified per step 240, this information is provided to the billing system 250, where bills are generated to be sent to payment organizations.

Figure 3:
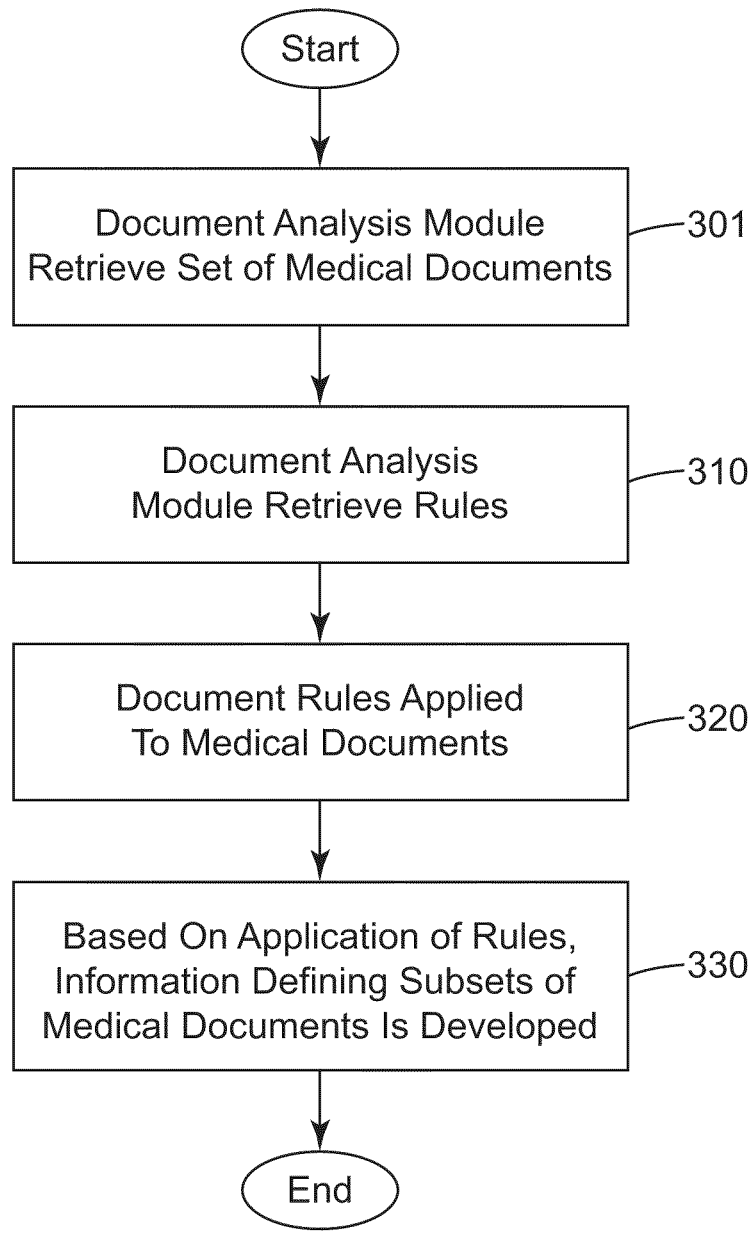
FIG. 3 is a high-level flowchart showing functionality of the MDAE system.
Figure 4:
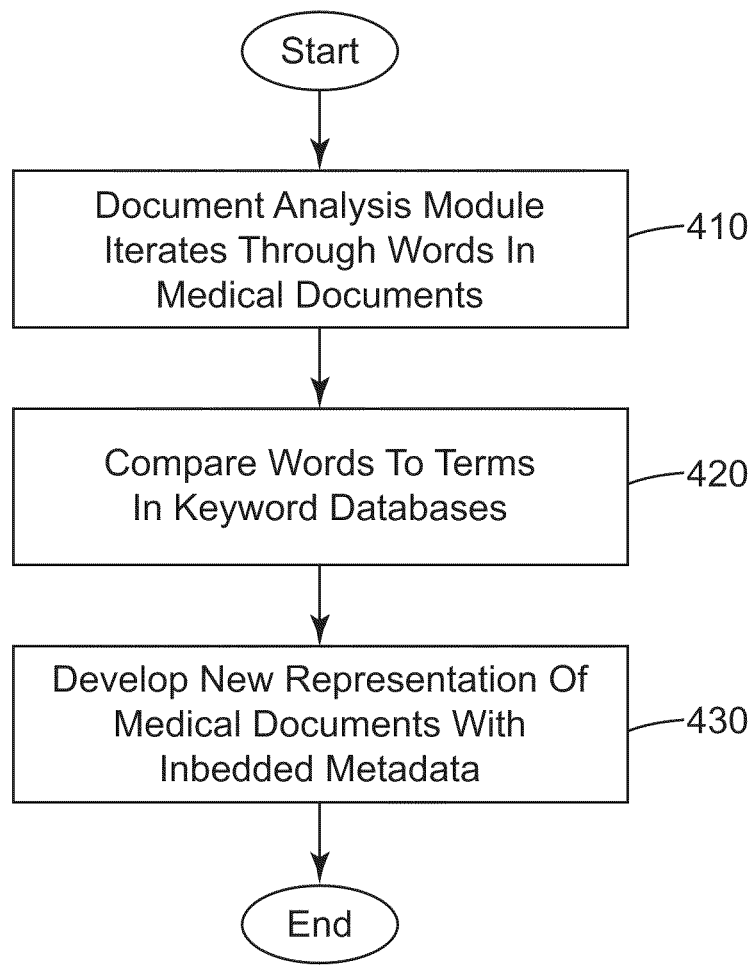
FIG. 4 is a high-level flowchart showing functionality of the MDAE system.

FIGS. 3 and 4 are flowcharts showing representative process steps involved in analyzing medical documentation 215. Per the architecture shown with respect to FIG. 1, these process steps would be facilitated by document analysis module 2. As earlier discussed, for a given set of documents associated with a patient encounter, document analysis module 2 has two objectives. The first objective is to identify subsets of the document relevant to coder 10. The second objective is to identify terms within the document that are relevant to coder 10, as well as associate various information relevant to interfacing, for particular terms, with the healthcare organization coding system 12. Though discussed in a particular sequence (objective 1 before objective 2), this is a design choice. In certain embodiments, objective 2 is first pursued, which then provides useful information for particular configurations of objective 1. For example, the fact of a high incidence of relevant terminology may mean that a particular subset of a document is identified. Alternatively, or in addition to, the healthcare organization may simply determine that particular documents, or particular subsections of documents, should always be displayed by user interface module 4. In such case, commensurate rules would be defined in MDEA rules database 7.

The process outlined in FIG. 3 starts with the document analysis module 2 retrieving a set of documents associated with a patient's encounter with a healthcare organization (301). These documents are, in one embodiment, already assembled in medical documentation database 6. Next, the document analysis module retrieves a set of rules from the MDAE rules database 7 (310). Next, the documents are iteratively examined by document analysis module 2, and the rules applied (320). Finally, based on the application of the rules, information defining subsets of medical documents is developed (330). This information may include, for example, references to sections of particular documents, or multiple sections of particular documents. This information is provided to MDAE module 3 for further processing.

The process outlined in FIG. 4 assumes the documents are already retrieved from the medical documents database 6 (as was done in the first step in the process outlined in FIG. 3). Document analysis module 2 then iterates through each word in each document (410) and compares these words to terms in keyword database 5. If a match is found, additional information is retrieved from keyword database 5 concerning the nature of the matched term. For example, it may be a term directly matched with a single ICD diagnosis code. Or, it could be a term that is suggestive of one of several particular ICD diagnosis codes. Or, it could be a term that suggests the exclusion of a particular one of several ICD diagnosis codes. Information concerning these matched terms are imbedded into a new representation of the document. This information might include a term type (for example, in the accompanying FIGs showing screen shots, several species of terms are represented. A first is a term associated with an ICD code. A second is a term indicative of a negation—that is, words that should signal that a particular aspect of a disease is not present. A third species is a term associated with demographic data useful for coding. An example of this third species would be the doctor's name. A fourth species is a term associated with a procedure. Other term species relevant to coding could be developed.

Figure 5:
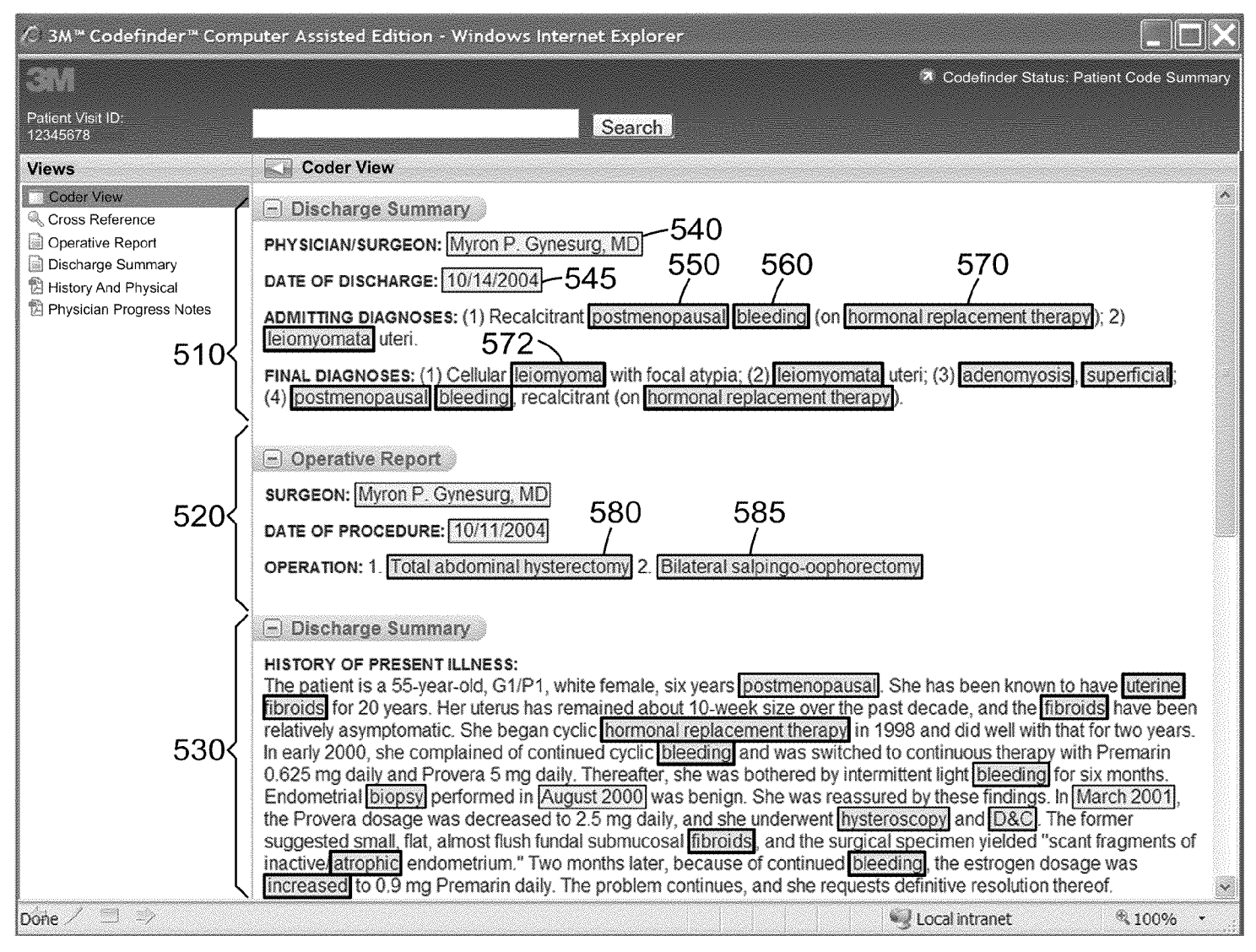

FIG. 5 is a rendering of a screen shot from MDAE system 1 as may be displayed to coder 10 via user interface module 4. In this rendering, document analysis module 2 has analyzed medical documents associated with a particular patient's encounter with a healthcare organization (as described above) and produced three medical document subsets (medical document subsets 510, 520, and 530). In this particular rendering, each of these document subsets is derived from a medical document. Rules in MDAE rules database 7 define the order of display of the document subsets, as well as the organization of the fields within each of the document subset sections.

The three document subsets 510, 520, and 530, include extracts from the medical documents on which they are based. Additionally, they may include field-type information to help organize portions of the medical documents. In the rendering of FIG. 5, visual indicia are associated with three separate species of terminology, per processes described above. The first terminology species associated with visual indicia in FIG. 5 is basic demographic data that is useful for coding. This includes the physician/surgeon name (field 540), as well as the discharge date (field 545). As can be seen, portions of the Discharge Summary view are field-based extracts (in other words, "Myron P. Gynesurg, MD" is pulled because it is associated with a particular field "PHYSICIAN/ SURGEON"). The field shown in the Discharge Summary view may map to actual fields on the original discharge summary document (or documents), which makes extraction a straightforward task. In other embodiments, where sought after information is not necessarily associated with field name and is instead loosely formatted, rules can be employed to make good guesses on the constituents of sought after information.

The visual indicia associated with the terminology species may be associated with the typeset (for example, different fonts, different levels of bolding, underlying, italicizing, and so forth). Also, specific terms may be highlighted or outlined with a colored box, the box in one embodiment defining an area that may be selected by coder 10 via a pointing device such as a mouse. Upon selection by coder 10, a further user interface display may be presented having more information, discussed below. However, even without additional functionality available upon selecting a term, or the visual indicia associated with a term, highlighting terms relevant to demographics, diseases, and procedures may be helpful for coder 10.

The second species of medical terminology associated with visual indicia in FIG. 5 are those terms potentially relevant to an ICD-defined disease (including disease-relevant terms 550, 560, 570, and 572). These include in the discharge summary document subset 510, the terms "postmenopausal" (550), "bleeding" (560), and "hormonal replacement therapy" (570).

The third species of medical terminology associated with visual indicia in FIG. 5 are those terms potentially relevant to an ICD-defined procedure (including procedure-relevant terms 580 and 585), such as "total abdominal hysterectomy" (580) and "bilateral salpingo-oophorectomy" (585).

Figure 6:
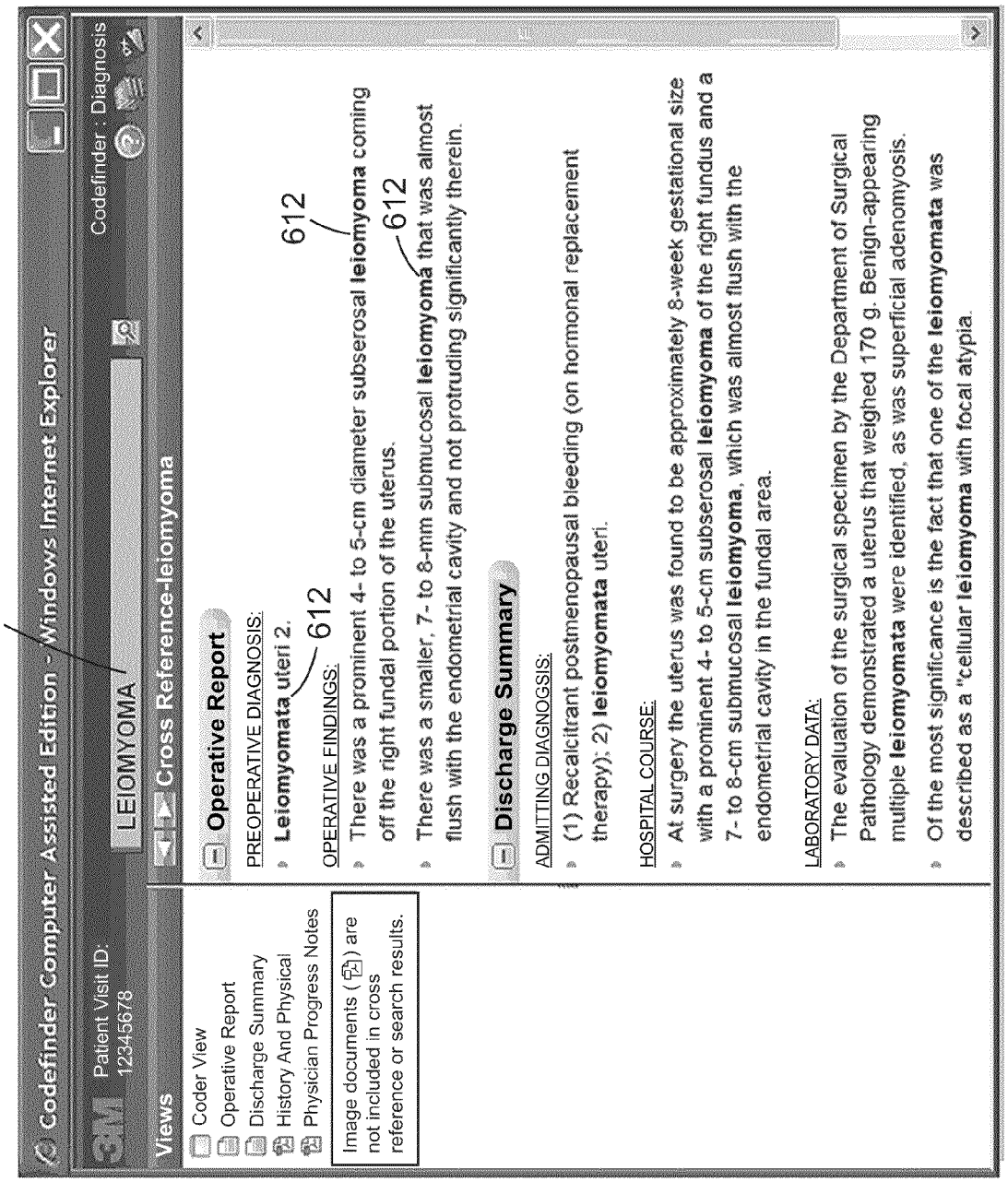
FIG. 6 is a screenshot from a user interface of the MDAE system.

FIG. 6 is a rendering of a screen shot from MDAE system 1 as is displayed after coder 10 has selected visual indicia associated with disease-relevant term "leiomyoma" (572), from the screenshot rendering in FIG. 5. This rendering is termed the diagnosis view, because it shows up upon selection of visual indicia associated with a diagnosis. Upon selection of a term from FIG. 5, the selected term is used in search box 610, and medical documents associated with the patient's encounter with the healthcare organization are searched. Common variations of the term are also included in the search (for example, a search for leiomyoma includes words that include additional characters, such as leiomyomata). In one embodiment, all available text-based documents are searched. Portions of the medical documents that include term matches are displayed, with the search term highlighted in the results.

Figure 7:
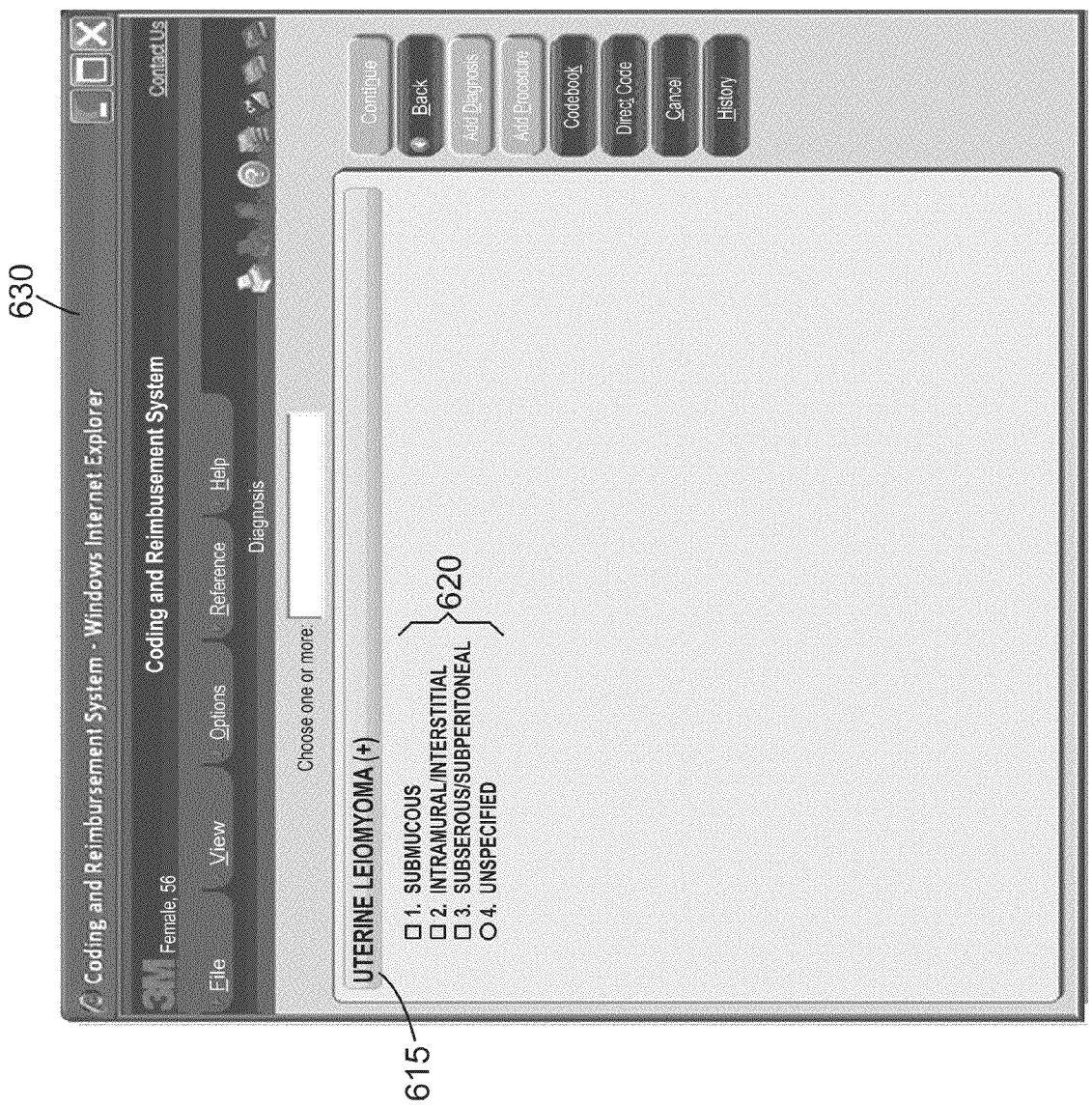
FIG. 7 is a screenshot from a user interface of the MDAE system.

FIG. 7 is a rendering of a screen shot from healthcare organization coding system 12. In this particular case, the screen shot is from commercially available "3M™ Coding and Reimbursement System" available from 3M™ HIS of Salt Lake City, Utah. Commensurate with the automatic search for a selected term described with respect to FIG. 6, information concerning the selected term is provided to the healthcare organization coding system 12. The particular information passed to healthcare organization coding system 12 may be tailored. In one embodiment, the MDAE system 1 has access to information concerning the disease and/or procedure hierarchy used by the healthcare organization coding system 12. In such case, MDAE system 1 may provide detailed information concerning where, in the healthcare organization coding system 12, coder 10 should be placed. On the other hand, in some embodiments, the selected term is provided to healthcare organization coding system 12, which in turn analyzes that term and determines on its own where in the coding process coder 10 should be placed. This latter approach treats the healthcare organization coding system 12 more akin to a black box. The passing of information between the MDAE system 1 and the healthcare organization coding system 12 may be accomplished in many ways. In one embodiment, a file is created by the MDAE system 1, which is then provided to the healthcare organization coding system 12. Other means of providing information between systems will be readily apparent to those skilled in the art.

Depending on the particular implementation details of the MDAE system and the healthcare organization coding system, different levels of information could be provided. For example, upon selection of particular terms, the MDAE system could provide additional terms that are known to be relevant to certain other aspects of the healthcare organization coding system. For example, in the example shown with respect to FIG. 5 and FIG. 7, FIG. 7 presents coder 10 with a screen soliciting input concerning species of uterine leiomyoma. If additional terms are present in the medical documents 6 that are suggestive of one of these, or suggestive of the exclusion of one of these, such information could be provided to healthcare organization coding system 12, and respective visual indicia associated with the suggested course (for example, if terms indicative of "submucous" are found to exist in the medical documentation, this term could be a special color, like green, whereas if terms are found suggesting the exclusion of intramural/interstitial, this term could be colored red, or even grayed out).

Figure 8:
FIG. 8 is a screenshot from a user interface of the MDAE system.

FIG. 8 is a rendering of the screen shot shown in FIG. 6, except that coder 10 has opted to search the medical documents for specific terms that the coder expects to be relevant to subsequent data entry in the healthcare organization coding system 12. For example, coder 10 may have seen the information presented in FIG. 7, and returned to the MDAE system to search for "submucous." Upon entering the characters, an alphabetized list of wildcard-type matches, along with the frequency of occurrence within the medical documentation, is displayed. As can be seen from the example, "submucosal" occurs three times, whereas subserosal occurs two times. This may indicate to coder 10 that each needs to be further investigated. If, however, submucosal occurred several times but subserous/subperitoneal occurred zero times, this may be enough for coder 10 to quickly conclude the uterine leiomyoma was of the submucous type.

Figure 9:
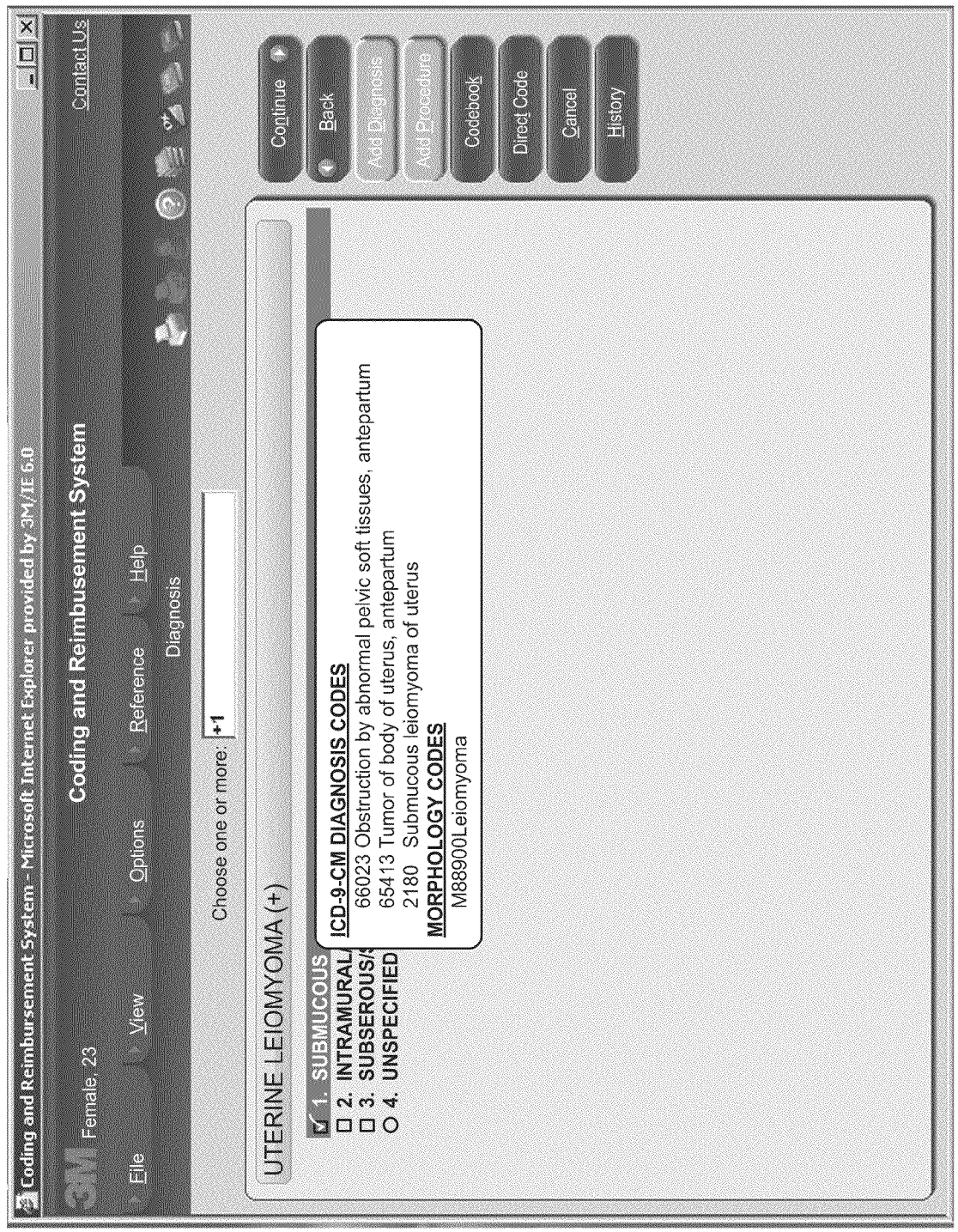
FIG. 9 is a screenshot from a user interface of the MDAE system.

FIG. 9 is a rendering of a screenshot of healthcare organization coding system 12 following coder 10's selection of "submucous." Specific ICD diagnosis codes are presented to coder 10, who may select a particular one. At this point, an ICD diagnosis code has been arrived at, and coder 10 can proceed with the next coding task.

Figure 10:
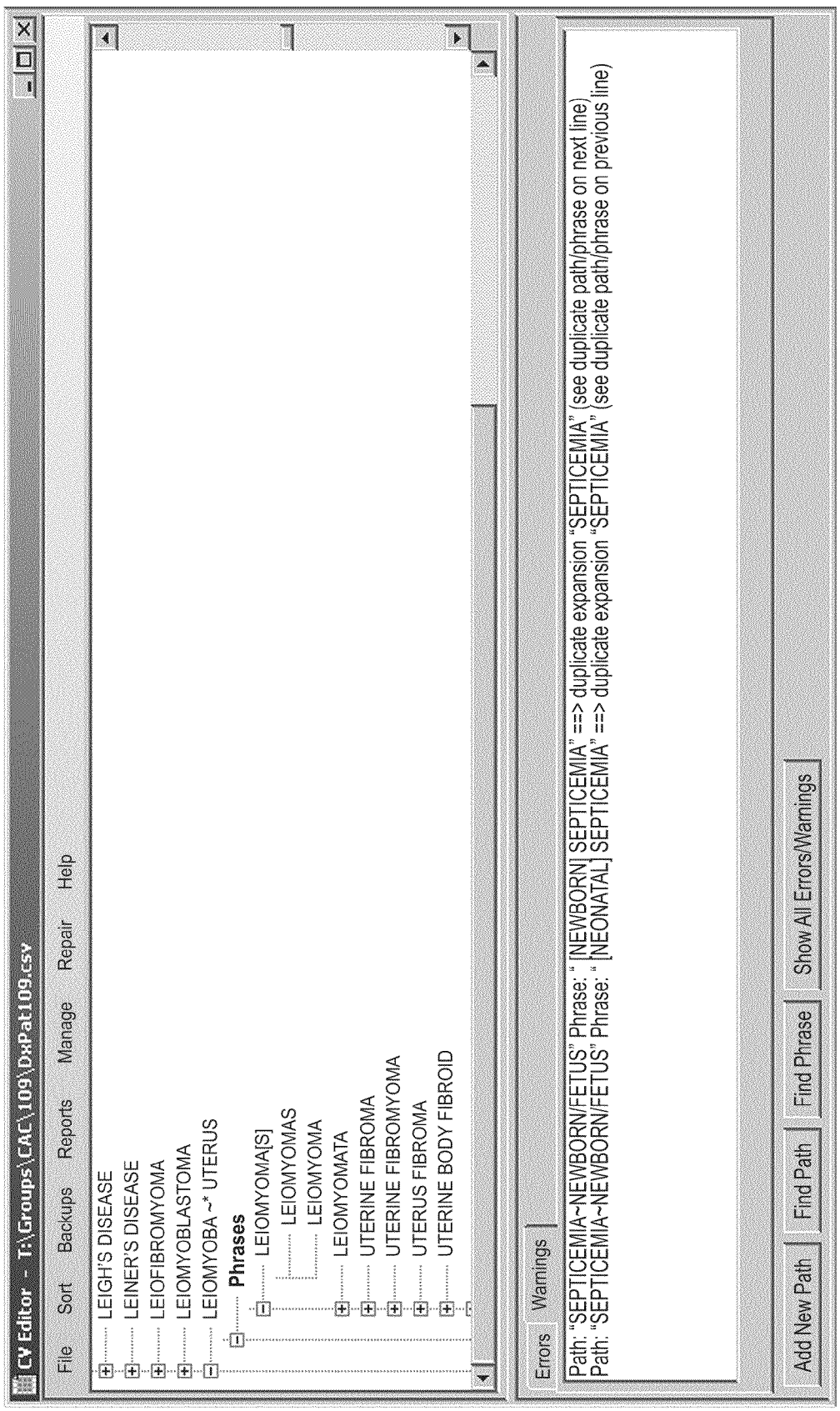
FIG. 10 is a screenshot from a utility that helps manage keywords.

FIG. 10 is a view of a tool used to manage keywords contained in keyword database 5. This tool allows management of relevant clinical terms used in the documentation extraction and analysis process. In the embodiment shown in FIG. 10, there is a close association between the keywords and the healthcare organization coding system—that is, the first order terms (such as LEIOMYOBA) may come directly from the healthcare organization coding system, then variations on the term are identified under "PHRASES."

Many modifications and other embodiments of the invention will come to mind to one skilled in the art to which this invention pertains, having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
receiving, by a computer having a processor and memory, a plurality of electronic documents associated with a patient's encounter with a healthcare organization;
automatically identifying, by the processor, terms in the plurality of electronic documents that are relevant to the patient's diagnosis or a procedure associated with the patient, wherein identifying terms comprises comparing terms within the plurality of electronic documents to terms in a database of terms;
displaying in a user interface communicatively coupled to the computer at least portions of the plurality of electronic documents with first visual indicia associated with the identified terms;
receiving selection input associated with at least one of the identified terms;
upon receipt of the selection input, providing information indicative of the selection input to a coding system that facilitates assignment of codes to aspects of a patient's encounter with a healthcare organization;
after providing the information indicative of the selection input to the coding system, receiving from the coding system information indicative of whether the identified term has been associated with a code; and
after receiving from the coding system information indicative of whether the identified term has been associated with a code, updating the user interface such that at least some terms associated with the assigned code are associated with a second visual indicia, wherein the first and second visual indicia appear differently to a user when displayed in the user interface.

2. The computer-implemented method of claim 1, further comprising:
upon receipt of the selection input, displaying other portions of at least some of the electronic documents that contain identified terms associated with the selection input.

3. The computer-implemented method of claim 1, wherein aspects of a patient's encounter comprise diseases and procedures.

4. The computer-implemented method of claim 1, wherein the codes assigned via the coding system are ICD-based codes.

5. A system comprising one or more microprocessors and memory, which executes software to cause the system to:
receive a plurality of electronic documents associated with a patient's encounter with a healthcare organization;
identify terms in the plurality of electronic documents that are relevant to the patient's diagnosis or a procedure associated with the patient, wherein identifying terms comprises comparing terms within the plurality of electronic document to terms in a database of terms;
display in a user interface at least portions of the plurality of electronic documents with first visual indicia associated with the identified terms;
receive selection input associated with at least one of the identified terms;
upon receipt of the selection input, provide information indicative of the selection input to a coding system that facilitates assignment of codes to aspects of a patient's encounter with a healthcare organization;
after providing the information indicative of the selection input to the coding system, receive from the coding system information indicative of whether the identified term has been associated with a code; and
after receiving from the coding system information indicative of whether the identified term has been associated with a code, updating the user interface such that at least some terms associated with the assigned code are associated with a second visual indicia, wherein the first and second visual indicia appear differently to a user when displayed in the user interface.

6. The system of claim 5, wherein the software further causes the system to:
upon receipt of the selection input, display other portions of at least some of the electronic documents that contain identified terms associated with the selection input.

7. The system of claim 5, wherein aspects of a patient's encounter comprise diseases and procedures.

8. The system of claim 5 wherein the codes assigned via the coding system are ICD-based codes.

9. A non-transitory computer-readable medium comprising instructions stored thereon, which upon execution, cause one or more processors to:
receive a plurality of electronic documents associated with a patient's encounter with a healthcare organization;
automatically identify terms in the plurality of electronic documents that are relevant to the patient's diagnosis or a procedure associated with the patient, wherein identifying terms comprises comparing terms within the plurality of electronic documents to terms in a database of terms;
cause display, in a user interface communicatively coupled to the one or more processors, of at least portions of the plurality of electronic documents with first visual indicia associated with the identified terms;
receive selection input associated with at least one of the identified terms;
upon receipt of the selection input, provide information indicative of the selection input to a coding system that facilitates assignment of codes to aspects of a patient's encounter with a healthcare organization;
after providing the information indicative of the selection input to the coding system, receive from the coding system information indicative of whether the identified term has been associated with a code; and
after receiving from the coding system information indicative of whether the identified term has been associated with a code, update the user interface such that at least some terms associated with the assigned code are associated with a second visual indicia, wherein the first and second visual indicia appear differently to a user when displayed in the user interface.

10. The non-transitory computer-readable medium of claim 9, further comprising instruction that upon execution cause the one or more processors to:
upon receipt of the selection input, cause display of other portions of at least some of the electronic documents that contain identified terms associated with the selection input.

11. The non-transitory computer-readable medium of claim 9, wherein aspects of a patient's encounter comprise diseases and procedures.

12. The non-transitory computer-readable medium of claim 9, wherein the codes assigned via the coding system are ICD-based codes.

13. The computer-implemented method of claim 1, wherein the coding system, after receiving information indicative of the selection input, solicits information from a user related to potential codes.

14. The computer-implemented method of claim 1, wherein the coding system, after receiving information indicative of the selection input, uses at least the information indicative of the selection input to satisfy one or more coding-related inquiries.

15. The computer-implemented method of claim 14, wherein the coding system, after satisfying the one or more coding-related inquiries, solicits additional input from a user related to further coding-related inquiries.

16. The computer-implemented method of claim 1, wherein the coding system, after receiving information indicative of the selection input, solicits a code selection input from the user associated with a diagnosis, procedure or condition related to the selection input.

17. The computer-implemented method of claim 16, wherein the code selection input comprises information from the user that assists with the assignment of the code.

18. The computer-implemented method of claim 17, further comprising: assigning, by the coding system, codes that are consistent with the code selection input.

19. The computer-implemented method of claim 1, wherein the codes assigned via the coding system are procedure codes.

20. The computer-implemented method of claim 1, wherein the codes assigned via the coding system are diagnosis codes.

21. The system of claim 5, wherein the software causes the system to, after receiving information indicative of the selection input, solicit information from a user related to potential codes.

22. The system of claim 5, wherein the software causes the system to, after receiving information indicative of the selection input, use at least the information indicative of the selection input to satisfy one or more coding-related inquiries.

23. The system of claim 22, wherein the software causes the system to, after satisfying the one or more coding-related inquiries, solicit additional input from a user related to further coding-related inquiries.

24. The system of claim 5, wherein the software causes the system to, after receiving information indicative of the selection input, solicit a code selection input from the user associated with a diagnosis, procedure or condition related to the selection input.

25. The system of claim 24, wherein the code selection input comprises information from the user that assists with the assignment of the code.

26. The system of claim 5, wherein the software causes the system to:
assign codes that are consistent with the code selection input.

27. The system of claim 5, wherein the codes assigned via the coding system are procedure codes.

28. The system of claim 5, wherein the codes assigned via the coding system are diagnosis codes.

29. The non-transitory computer-readable medium of claim 9, wherein the instructions cause the one or more processors to, after receiving information indicative of the selection input, solicit information from a user related to potential codes.

30. The non-transitory computer-readable medium of claim 9, wherein the instructions cause the one or more processors to, after receiving information indicative of the selection input, use at least the information indicative of the selection input to satisfy one or more coding-related inquiries.

31. The non-transitory computer-readable medium of claim 30, wherein the instructions cause the one or more processors to, after satisfying the one or more coding-related inquiries, solicit additional input from a user related to further coding-related inquiries.

32. The non-transitory computer-readable medium of claim 9, wherein the instructions cause the one or more processors to, after receiving information indicative of the selection input, solicit a code selection input from the user associated with a diagnosis, procedure or condition related to the selection input.

33. The non-transitory computer-readable medium of claim 32, wherein the code selection input comprises information from the user that assists with the assignment of the code.

34. The non-transitory computer-readable medium of claim 9, wherein the instructions cause the one or more processors to:
assign codes that are consistent with the code selection input.

35. The non-transitory computer-readable medium of claim 9, wherein the codes assigned via the coding system are procedure codes.

36. The non-transitory computer-readable medium of claim 9, wherein the codes assigned via the coding system are diagnosis codes.

* * * * *

UNITED STATES PATENT AND TRADEMARK OFFICE
CERTIFICATE OF CORRECTION

PATENT NO. : 8,600,772 B2  
APPLICATION NO. : 12/473975  
DATED : December 3, 2013  
INVENTOR(S) : David Bacon Page 1 of 1

It is certified that error appears in the above-identified patent and that said Letters Patent is hereby corrected as shown below:

In the Drawings

<u>Drawings, Sheet 4 of 10</u>
Fig. 4, Reference Number 430, delete "Inbedded" and insert -- Embedded --, therefor.

In the Specification

<u>Column 8</u>
Line 62, delete "LEIOMYOBA)" and insert -- LEIOMYOMA) --, therefor.

Signed and Sealed this
Twenty-ninth Day of July, 2014

Michelle K. Lee
*Deputy Director of the United States Patent and Trademark Office*